(12) United States Patent
Hsu et al.

(10) Patent No.: US 8,658,181 B2
(45) Date of Patent: Feb. 25, 2014

(54) PHARMACEUTICAL COMPOSITION FOR PREVENTING AND TREATING LIVER FIBROSIS OR NONALCOHOLIC FATTY LIVER DISEASE

(71) Applicant: TCM Biotech International Corp., Taipei (TW)

(72) Inventors: Huan Ching Hsu, Taipei (TW); Ya Chun Wang, Taipei (TW)

(73) Assignee: TCM Biotech International Corp., Taipei (TW)

( * ) Notice: Subject to any disclaimer, the term of this patent is extended or adjusted under 35 U.S.C. 154(b) by 0 days.

(21) Appl. No.: 13/664,550

(22) Filed: Oct. 31, 2012

(65) Prior Publication Data
US 2013/0259894 A1    Oct. 3, 2013

(30) Foreign Application Priority Data

Mar. 28, 2012   (TW) .............................. 101110713 A

(51) Int. Cl.
A61K 36/481   (2006.01)
A61K 36/068   (2006.01)
A61K 36/00    (2006.01)
A61K 36/06    (2006.01)

(52) U.S. Cl.
USPC ...................................... 424/195.15; 424/725

(58) Field of Classification Search
None
See application file for complete search history.

Primary Examiner — Qiuwen Mi
(74) Attorney, Agent, or Firm — Woodard, Emhardt, Moriarty, McNett & Henry LLP

(57) ABSTRACT

The present invention provides a pharmaceutical composition for preventing and treating liver fibrosis or nonalcoholic fatty liver disease, comprising 50 to 90% by weight of *Cordyceps sinensis* mycelium powder, and 10 to 50% by weight of condensed astragalus powder.

6 Claims, 6 Drawing Sheets

(A)

(B)

PHARMACEUTICAL COMPOSITION FOR PREVENTING AND TREATING LIVER FIBROSIS OR NONALCOHOLIC FATTY LIVER DISEASE

FIELD OF THE INVENTION

The present invention provides a pharmaceutical composition for preventing and treating liver fibrosis or nonalcoholic fatty liver disease, comprising 50 to 90% by weight of *Cordyceps sinensis* mycelium, and 10 to 50% by weight of astragalus.

BACKGROUND OF THE INVENTION

Chronic liver injury caused by alcohol, virus or chemical substance may induce the activation of hepatic stellate cell for secreting a large amount of extracellular matrix such as collagen, which may lead to liver fibrosis as a consequence of the extracellular matrix over-deposition. With regard to the above pathogenic mechanism, drug development for treating liver fibrosis is mainly directed to a target of inhibiting extracellular matrix synthesis, or accelerating extracellular matrix degradation. However, most of the substances discovered so far have shown biotoxicity or strong side effect, and none has been found effective in animal models.

Nonalcoholic fatty liver disease (NAFLD) relates to a disease afflicting patients who did not consume excessive alcohol, with their liver fat content of 5% or more by weight of the whole liver weight. Clinically, patients with NAFLD usually accompany with obesity, diabetes, hyperlipidemia and the like, and are likely to develop liver fibrosis and liver cirrhosis. At present, nonalcoholic fatty liver disease is treated by controlling the patient's weight, blood glucose and blood lipid. Yet, there is not any medicine found effective for treating nonalcoholic fatty liver disease, and further preventing the progression of liver fibrosis and liver cirrhosis.

SUMMARY OF THE INVENTION

The present invention provides a pharmaceutical composition for preventing and treating liver fibrosis or nonalcoholic fatty liver disease, comprising 50 to 90% by weight of *Cordyceps sinensis* mycelium, and 10 to 50% by weight of astragalus.

*Cordyceps sinensis* is used as a traditional Chinese medicine, possessing the effects such as antimicrobial, anti-inflammatory, antifebrile, sedation, promoting hemangiectasis, relieving asthma, antiarrhythmia, promoting metabolism, anti-aging, anti-tumor and immune-stimulatory. Since wild *Cordyceps sinensis* is very rare and expensive, *Cordyceps sinensis* of the present invention as used is a purified *Cordyceps sinensis* mycelium, including the following strains: *Hirsutella sinensis, Paecilomyces sinensis, Chrysosporium sinensis, Sporothrix insectorum, Stachybotrys* sp., *Tolypocladium sinensis, Paecilomyces hepiali* and *Hirsutella hepiali*, etc.

According to a preferred embodiment of the invention, *Cordyceps sinensis* mycelium is obtained by an isolated cultured and fermented *Paecilomyces hepiali* Chen et Dai mycelium. Said mycelium is then freeze-dried or bake-dried to produce a powdery form as a main component of the pharmaceutical composition of the invention.

The medicinal portion of astragalus (*Astragalus membranaceus*) is its root, which possesses the effect of enhancing cell mediated immunity. The condensed *astragalus* powder of the present invention is made of the dried roots selected from *Astragalus membranaceus* (Fisch.) Bge. Var. *mongholicus* (Bge.) Hsiao or *Astragalus membranaceus* (Fisch.) Bge., as another main component of the pharmaceutical composition of the invention. Any of the other astragalus species also belongs to the field of the invention.

The pharmaceutical composition of the present invention further comprises a condensed powder of Zizyphi Sativae, and more further comprises the pharmaceutically acceptable excipeints. The excipients may be selected from one or more of the group consisting of tribasic calcium phosphate, zinc gluconate, magnesium stearate, silicon dioxide, and starch.

Another purpose of the invention is to provide a pharmaceutical composition for the preparation of a medicament or a health food for preventing and treating liver fibrosis or nonalcoholic fatty liver disease. The medicament or the health food may be an oral preparation in the form of capsules, tablets or pulvis.

Implementation of a preferred embodiment and the advantageous effect for preventing and treating liver fibrosis or nonalcoholic fatty liver disease according to the invention are hereunder described in more details.

DETAILED DESCRIPTION OF THE INVENTION

The pharmaceutical composition and methods of the present invention will be described below in detail with reference to the following embodiments, and also as set forth in applicants' Taiwanese priority application No. 101110713, filed Mar. 28, 2012, the entire contents of which are hereby incorporated herein by reference. However, these embodiments are used mainly to assist in understanding the present invention, but not to restrict the scope of the present invention. Various possible modifications and alterations could be conceived of by one skilled in the art to the form and the content of any particular embodiment, without departing from the spirit and scope of the present invention, which is intended to be defined by the appended claims.

Preparation of the Pharmaceutical Composition of the Invention

Figure 1:
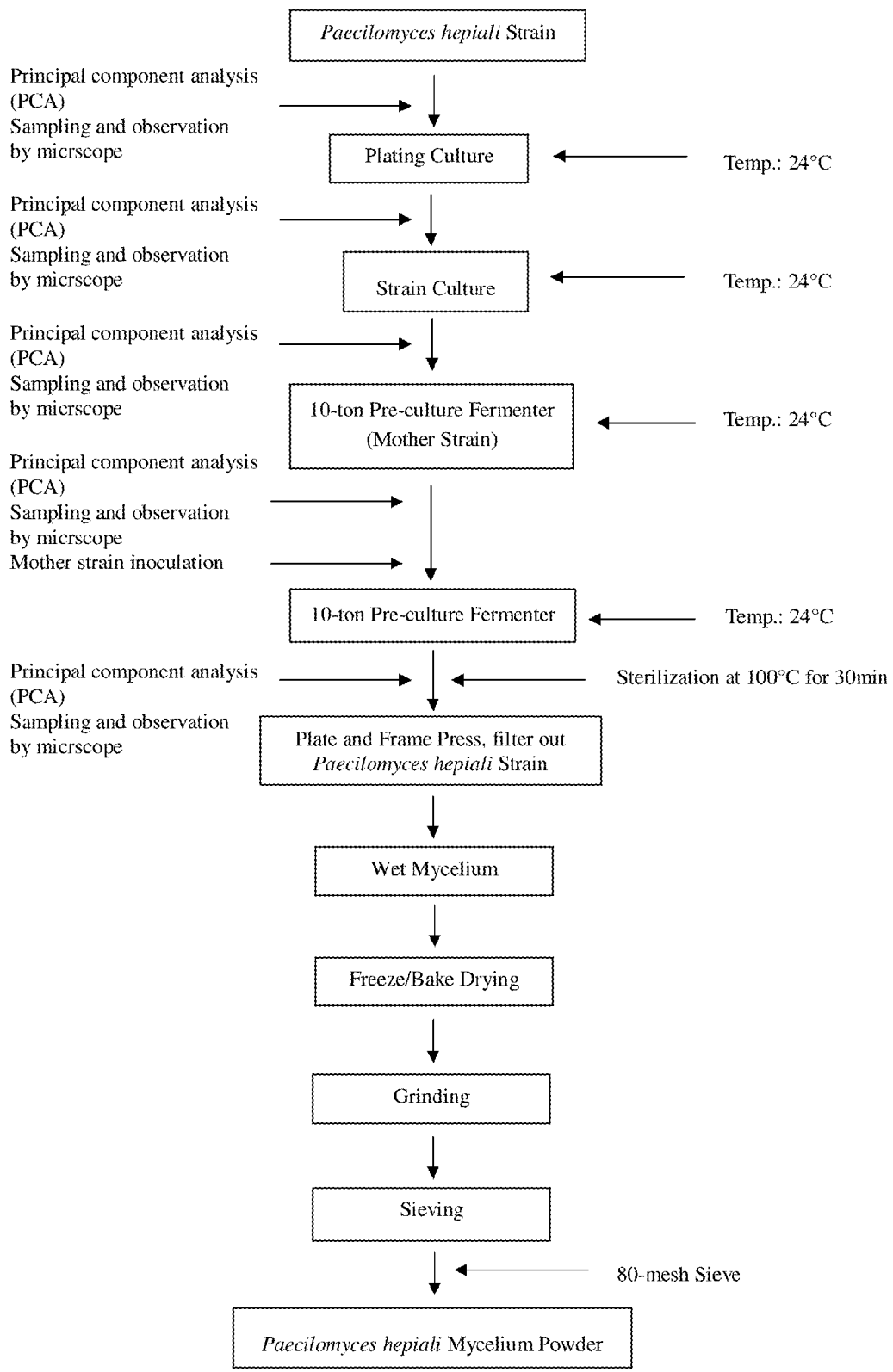
FIG. 1 shows a flow chart of the preparation of *Paecilomyces hepiali* mycelium powder.

In one preferred embodiment, *Paecilomyces hepiali* Chen et Dai mycelium powder is used as the *Cordyceps sinensis* mycelium. FIG. 1 illustrates a flow chart of the preparation of *Paecilomyces hepiali* Chen et Dai mycelium powder. The strain of *Paecilomyces hepiali* is cultured and fermented, and then the harvested mycelium is freeze-dried or bake-dried, ground and sieved, so as to produce a powdery form. Further, a commercially available condensed astragalus powder made of the dried roots selected from *Astragalus membranaceus* (Fisch.) Bge. Var. *mongholicus* (Bge.) Hsiao and *Astragalus membranaceus* (Fisch.) Bge. is used. In addition, the pharmaceutical composition of the invention further comprises a condensed Zizyphi Sativae powder and pharmaceutically acceptable excipients. The excipients may be selected from one or more of the group consisting of tribasic calcium phosphate, zinc gluconate, magnesium stearate, silicon dioxide, and starch. The preferred composition is in a form of a capsule. Each ingredient and the content contained therein are listed as follows:

| Ingredients | mg/capsule | | |
|---|---|---|---|
| *Paecilomyces hepiali* Chen et Dai *mycelium* powder | 275 | 350 | 450 |
| Condensed *astragalus* powder | 200 | 125 | 45 |
| Condensed Zizyphi Sativae powder | 20 | 20 | — |
| Excipients | 25 | 25 | 25 |
| Total | 520 | 520 | 520 |

Human dose (70 kg) of the composition of invention is 3120 mg/day. Rat oral dose is calculated based on the equivalent dose rate by a surface area ratio of the experimental animal to human. The surface area ratio of a 200 g rat to a 70 kg human is 0.018, and thus the convert dosage to the rat of 200 g is 56.16 mg/day. The effects of the composition of the invention for preventing and treating liver fibrosis and nonalcoholic fatty liver disease will be determined as follows.

Protection from Liver Fibrosis Induced by Thioacetamide (TAA)

Five weeks old male Wistar rats are divided into four groups for the following treatments:

| Groups | Administration substance and its dose |
|---|---|
| Normal control | Inject saline, feed deionized water |
| Negative control | Inject TAA, feed deionized water |
| Normal dosage | Inject TAA, feed 280.8 mg/kg/day of the composition of invention |
| High dosage | Inject TAA, feed 1404 mg/kg/day of the composition of invention |

The rats were injected with 100 mg/kg of TAA three times a week to induce liver fibrosis symptom. Each group of the rats was fed with deionized water, an one time dose or a five times dose composition of invention, respectively, six times a week for a period of 8 weeks.

After 8 weeks, collect the blood of the rats in each group for determining liver-injury related biochemical index and the blood lipid in the serum, and determining the lipid contents, cytokines, collagens, antioxidant enzyme activities and peroxidative metabolite in the liver tissues. The results are described, respectively, as follows:

1. Effects of the Biochemical Value in Blood and the Lipid Content in Liver.

Figure 2:
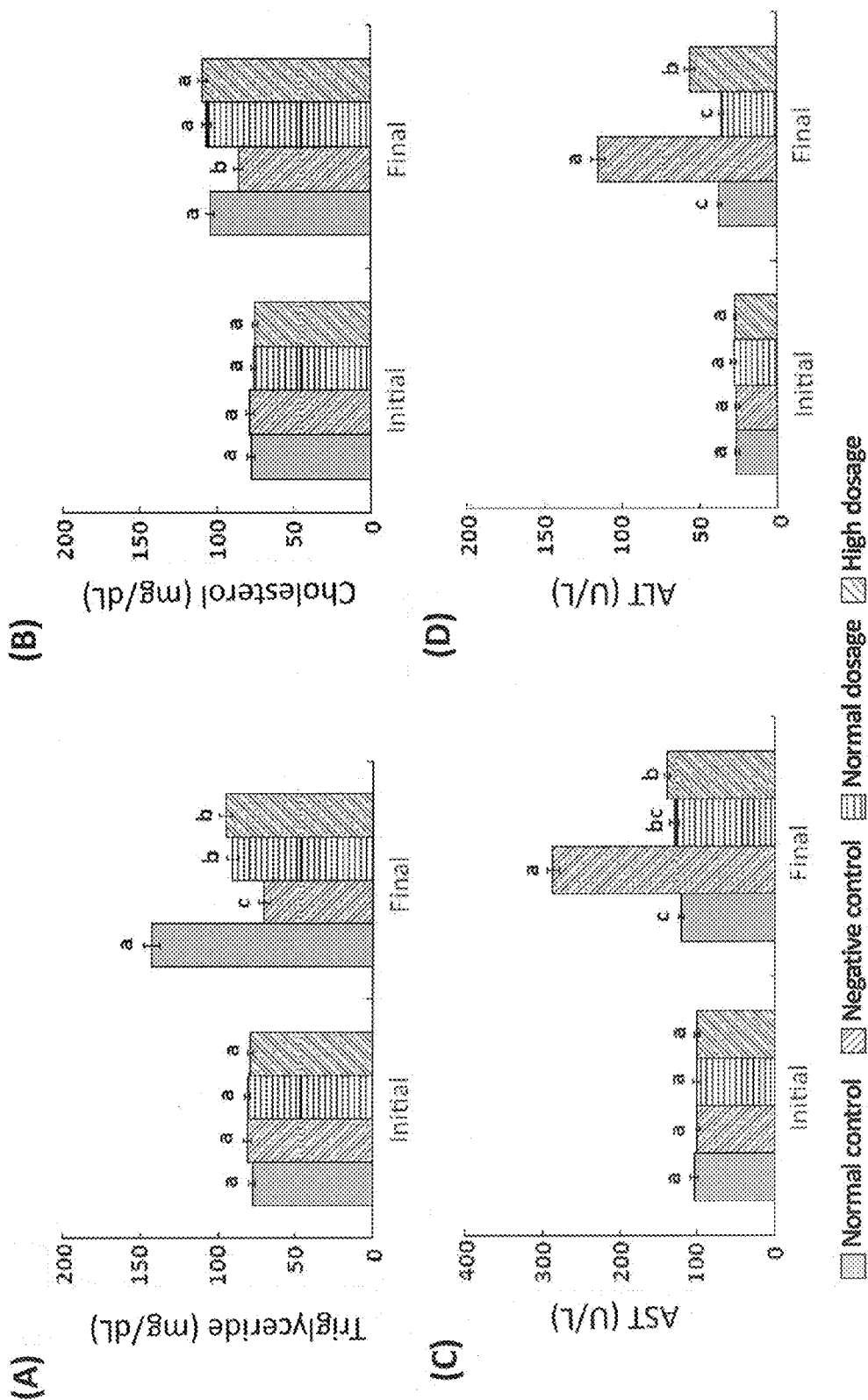
FIG. 2 shows the triglyceride (A), cholesterol (B), AST (C) and ALT (D) levels determined by an experiment of TAA induced liver fibrosis with four treatments. The data are given as means±SEM (n=12). Different letters indicate significant differences ($p<0.05$).

As illustrated in FIG. 2A and FIG. 2B, TAA treatment leads to a decrease of blood lipid (triglyceride (TG) and cholesterol (TC)). TG and TC contents in the serum of the subjects supplemented with the composition of the invention are significantly higher than that of the subjects treated by TAA only. TC can even return to the level as that in the control group. The analytical result for the liver lipid demonstrates that supplement of the composition of the invention may effectively reduce the accumulation of lipids in liver (as shown in Table 1).

TABLE 1

| Liver lipid | Treatment | | | |
|---|---|---|---|---|
| (mg/g liver) | Normal control | Negative control | Normal dosage | High dosage |
| Triglyceride | 10.29 ± 0.07b | 11.56 ± 0.29a | 10.12 ± 0.15b | 10.06 ± 0.28b |
| Cholesterol | 2.44 ± 0.07c | 4.51 ± 0.08a | 2.76 ± 0.11b | 2.70 ± 0.09b |

The data in the table are given as means ± SEM (n = 12). Mean values with different letters in each testing parameter were significant different ($p < 0.05$).

2. Effects of the Antioxidant Capacity of Liver.

Results for determining the antioxidant ingredient and enzyme activities were shown in Table 2.

TABLE 2

| | Treatment | | | |
|---|---|---|---|---|
| | Normal control | Negative control | Normal dosage | High dosage |
| MDA (nmol/mg protein) | 0.45 ± 0.02c | 2.38 ± 0.04a | 1.62 ± 0.05b | 1.63 ± 0.06b |
| TEAC (nmol/mg protein) | 100.18 ± 3.11a | 83.51 ± 3.04b | 108.87 ± 3.66a | 109.36 ± 4.98a |
| SOD (unit/mg protein) | 11.12 ± 0.41b | 4.35 ± 0.09c | 14.15 ± 0.19a | 10.64 ± 0.26b |
| CAT (unit/mg protein) | 19.72 ± 0.39b | 17.38 ± 0.36c | 20.83 ± 0.43ab | 20.97 ± 0.38a |

TABLE 2-continued

| | Treatment | | | |
|---|---|---|---|---|
| | Normal control | Negative control | Normal dosage | High dosage |
| GPx (nmol NADPH oxidized/min/mg protein) | 36.16 ± 0.79a | 23.54 ± 0.54d | 28.21 ± 0.55c | 30.71 ± 0.59b |

The data in the table are given as means ± SEM (n = 12). Mean values with different letters in each testing parameter were significant different ($p < 0.05$).

The result demonstrates that supplement of the composition of the invention significantly reduces lipid peroxide melondialdehyde (MDA), increases trolox equivalent antioxidant capacity (TEAC), and increases antioxidant enzyme (SOD, CAT, GPx) activities.

3. Effects of Liver Injury.

Alanine transaminase (ALT) and aspartate transaminase (AST) may be the indexes for liver injury. The result demonstrates that supplement of the composition of the invention efficaciously decreases the ALT and AST in blood (as shown in FIG. 2C and FIG. 2D), and the low dosage composition has also shown the ability to decrease ALT and AST.

Tumor necrosis factor-α (TNFα) and interleukin-1β (IL-1β) are cytokines secreted by the damaged liver cells, which may aggravate cell injury, and induce strong inflammatory responses. As shown in Table 3, the result demonstrates that supplement of the composition of the invention efficaciously decrease the contents of TNFα and IL-1β, and represents the reduced level of liver injury. In addition, as for the analysis of liver collagen, the supplement of the composition of the invention significantly reduces the content of the liver collagen (Table 3).

| Groups | Administration substance and its dose |
|---|---|
| Normal control | 1 ml/kg olive oil/10 ml/kg deionized water |
| Negative control | 1 ml/kg carbon tetrachloride/10 ml/kg deionized water |
| Normal dosage | 1 ml/kg carbon tetrachloride/286.2 mg/kg composition of invention |
| High dosage | 1 ml/kg carbon tetrachloride/2862 mg/kg composition of invention |
| Positive control | 1 ml/kg carbon tetrachloride/200 mg/kg Silymarin |

The rats were fed with 1 ml/kg 40% carbon tetrachloride dissolved in olive oil three times a week; and each group was fed daily with deionized water, an one time dose or a ten times dose composition of invention, and Silymarin, by oral administration for six weeks.

1. Blood Biochemical Value and the Assay.

After six weeks, collect the blood for determining each liver function illustrated in the following Table 4. The results show that administration of the composition of the invention can reduce AST, ALT and bilirubin, and increase the contents of serum albumin.

TABLE 3

| | | Treatment | | | |
|---|---|---|---|---|---|
| | | Normal control | Negative control | Normal dosage | High dosage |
| Cytokine (mg/g liver) | Interleukin-1β | 3.28 ± 0.12b | 5.03 ± 0.12a | 3.68 ± 0.20b | 3.73 ± 0.19b |
| | Tumor necrosis factor-α | 18.40 ± 0.98c | 26.00 ± 0.85a | 22.72 ± 0.84b | 22.02 ± 0.71b |
| Liver collagen content (g/g liver) | | 0.29 ± 0.14c | 0.43 ± 0.01a | 0.36 ± 0.01b | 0.35 ± 0.01b |

The data in the table are given as means ± SEM (n = 12). Mean values with different letters in each testing parameter were significant different ($p < 0.05$).

According to the above rat model of TAA induced liver fibrosis, the pharmaceutical composition of the invention can improve lipid metabolism in liver, reduce lipid accumulation, and increase antioxidant capacity, so as to alleviate liver injury caused by TAA. The desired effect may also be achieved even by the low dosage (normal dosage).

TABLE 4

| | AST (U/L) | ALT (U/L) | Bilirubin (μmole/L) | Serum albumin (g %) |
|---|---|---|---|---|
| Normal control | 89.7 ± 25.6 | 54.8 ± 9.9 | 0.1 ± 0.0 | 4.9 ± 0.0 |
| Negative control | 725.3 ± 326.6** | 710.8 ± 273.5** | 0.6 ± 0.3** | 4.3 ± 0.3** |
| Normal dosage | 90.5 ± 23.1 | 46.8 ± 15.7 | 0.1 ± 0.1** | 4.8 ± 0.2** |
| High dosage | 84.2 ± 13.3 | 51.2 ± 3.7 | 0.1 ± 0.0* | 4.8 ± 0.1** |
| Positive control | 93.0 ± 16.9 | 61.8 ± 11.9 | 0.2 ± 0.1** | 4.4 ± 0.2** |

*represents $p < 0.05$,
**represents $p < 0.01$, compared with the normal control Chemical Liver Injury Induced by Carbon Tetrachloride Sprague-Dawley rats are divided into five groups for the following treatments:

2. Antioxidant Enzyme and Protein Concentration.

The results for determining the activities of antioxidant molecules in the liver tissues, including glutathione (GSH), glutathione peroxidase (GSH-Px), glutathione reductase (GSH-Rd), superoxide dismutase (SOD) and catalase, are illustrated in Table 5.

TABLE 5

|  | GSH (μmole/g tissue) | Catalase (U/mg protein) | GSH-Px (U/mg protein) | SOD (U/mg protein) | GSH-Rd (U/mg protein) | Protein Con. (mg/g tissue) |
|---|---|---|---|---|---|---|
| Normal control (n = 6) | 4.7 ± 0.3 | 1286 ± 45.4 | 8.0 ± 0.2 | 12.7 ± 0.1 | 81.7 ± 1.8 | 94.5 ± 1.1 |
| Negative control (n = 6) | 4.4 ± 0.2 | 961 ± 47.7 | 5.3 ± 0.2 | 4.0 ± 0.4* | 69.5 ± 0.5 | 71.8 ± 1.1 |
| Normal dosage (n = 6) | 4.6 ± 0.2 | 1245 ± 13.1** | 7.5 ± 0.1 | 8.8 ± 0.2* | 75.8 ± 1.8 | 87.3 ± 2.3 |
| High dosage (n = 6) | 4.6 ± 0.1* | 1242 ± 18.0** | 6.0 ± 0.2 | 8.3 ± 0.2* | 76.5 ± 0.5 | 84.3 ± 1.0 |
| Positive control (n = 6) | 4.5 ± 0.1* | 1203 ± 55.1 | 7.3 ± 0.1* | 7.2 ± 0.2 | 74.5 ± 1.4 | 83.6 ± 1.9 |

*represents $p < 0.05$,
**represents $p < 0.01$, compared with the normal control The result shows that after administration of the composition of the invention, GSH and GSH-Px increase to the level near to the normal control group, catalase and SOD are raised to be higher than the positive control group of administrating Silymarin, and the protein concentration also shows the same tendency.

3. Pathological Section.

Coarse liver surface was observed from the pathological section of the liver injury induced by carbon tetrachloride. However, the liver tissue of the rats administrating the composition of the invention represents mild fibrosis, and the probability of hepatic lobules distortion may be reduced.

Distribution of collagen in liver tissues was observed by a histological stain of Sirius red. The liver tissue section of the negative control group treated with carbon tetrachloride shows an increased area of collagen, and the hepatic lobules has severe liver fibrosis. Result of the quantitative analysis is illustrated in Table 6, showing that both the dosages of the composition of the invention reduce the collagen in liver, and have the function to protect liver.

TABLE 6

|  | Ratio (%) |
|---|---|
| Normal control (n = 6) | 0.81 ± 0.37 |
| Negative control (n = 6) | 9.69 ± 4.98 |
| Normal dosage (n = 6) | 1.72 ± 0.38 |
| High dosage (n = 6) | 2.52 ± 1.07 |
| Positive control (n = 6) | 5.68 ± 4.00 |

According to the above rat model of carbon tetrachloride induced liver injury, the pharmaceutical composition of the invention demonstrates that the indexes for rat liver injury can be reduced, the antioxidant enzyme activity and protein concentration are increased. Also, the pathological section and the collagen content illustrate the phenomenon of liver fibrosis reduction.

Evaluation on the Effect of Fatty Liver Disease Induced by High Fat Diet

Six weeks old C57BL/6 mice were fed with high fat diet containing 60 kcal % or more of fat (D12492, Research Diets, USA) for 18 weeks, to induce mice obesity; and the same aged mice were fed with normal diet containing 10 kcal % fat (D12450B, Research Diets, USA) as a control group.

Each group of the mice was orally administered with sterile water (10 ml/kg), or the composition of the invention (557 mg/kg or 2786 mg/kg), respectively, five times a week for ten weeks. The mice were weighed each week. After ten weeks, collect the blood for determining AST, ALT and insulin in serum, resect the liver and weigh.

Figure 3:
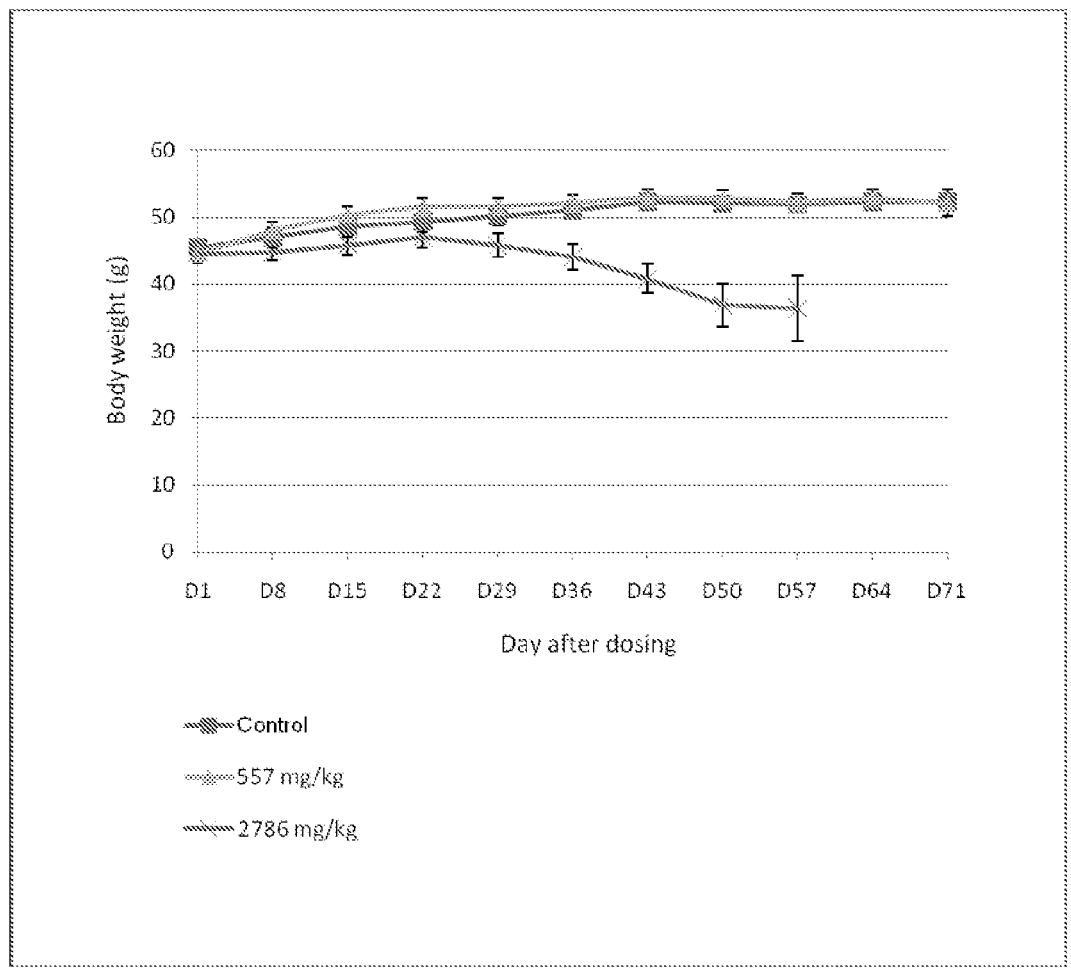
FIG. 3 shows the change of mice weight determined by an experiment of high fat diet induced fatty liver disease with the treatments of a control group and two doses (557 and 2786 mg/kg).

Body weights of the mice fed with normal diet in the blank group have no significant variation during the entire experimental period; and body weights of the mice fed with high fat diet in the control group are statistically significantly higher than those of the blank group. There is no significant difference in the body weights when comparing the 557 mg/kg composition of invention with the control group. It can be observed that the body weights of the mice orally administered with high dosage (2786 mg/kg) decrease from the $22^{nd}$ day of dosing; and significantly decrease from the $36^{th}$ to $57^{th}$ day (FIG. 3).

Figure 4:
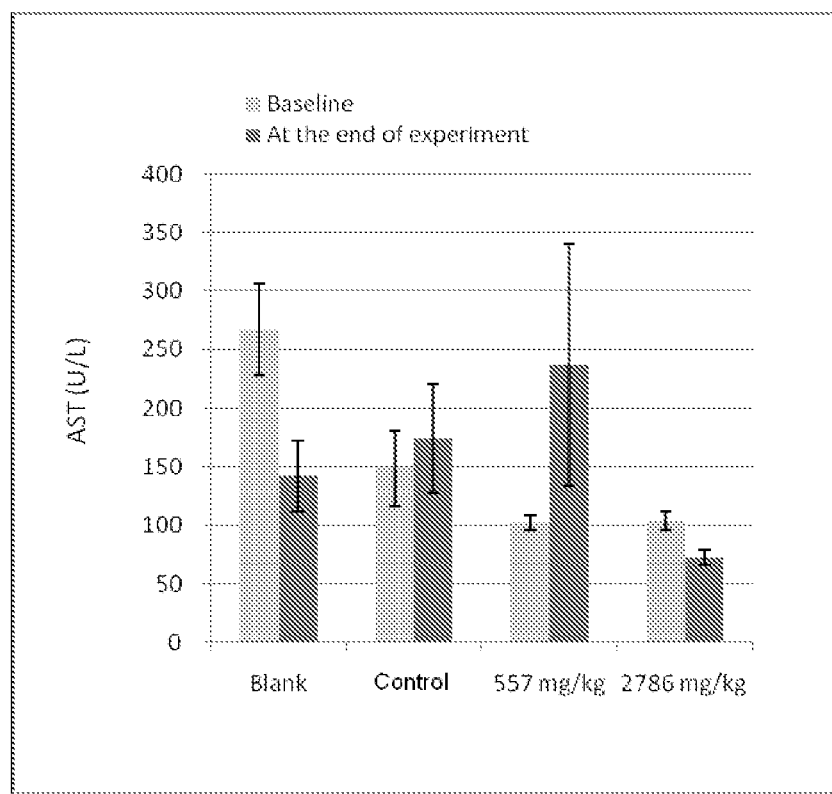
FIG. 4 shows the AST (A) and ALT (B) levels determined by an experiment of high fat diet induced fatty liver disease with four treatments.
Figure 4:
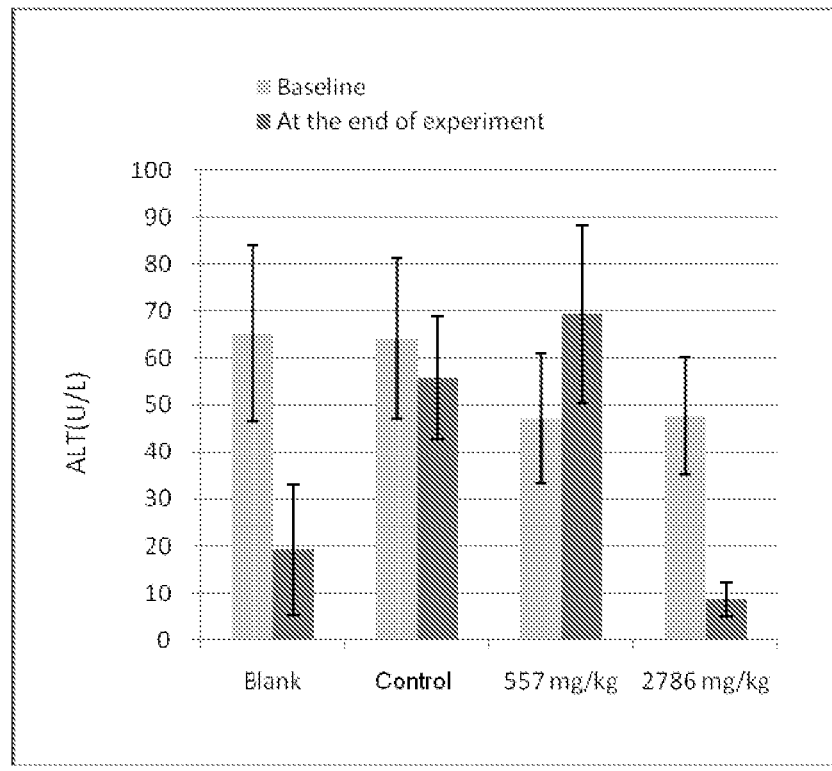

After orally administering the mice with the composition of invention in high dosage 2786 mg/kg for eight weeks, AST level (73±6.6 U/L) in serum decreased by about 58% when comparing with the control group (174±46.7 U/L). In particular, ALT level (9±3.7 U/L) significantly decreased by about 84% (as the control group of 56±13.2 U/L, $p<0.05$) (FIG. 4A and FIG. 4B), which has statistical difference.

Figure 5:
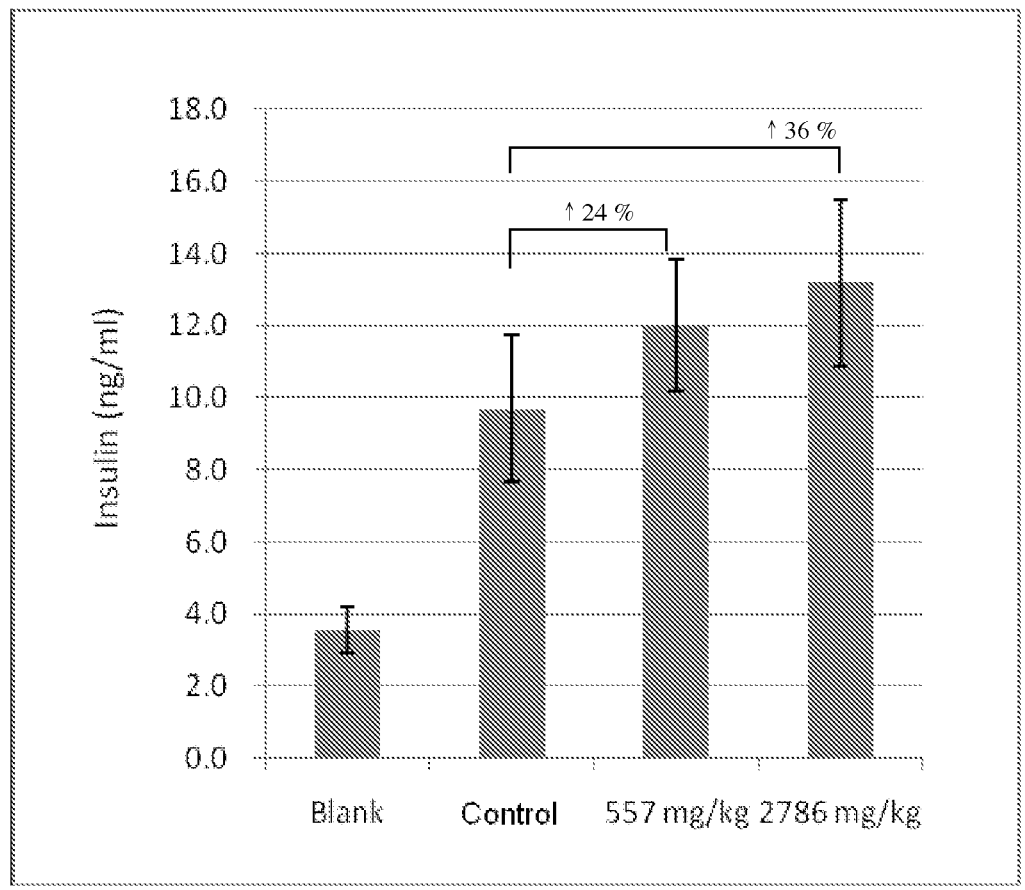
FIG. 5 shows the insulin contents determined by an experiment of high fat diet induced fatty liver disease with four treatments.

Insulin level (9.69±2.04 ng/ml) of the mice fed with high fat diet is 2.7 times higher than that of the mice fed with normal diet (3.55±0.65 ng/ml). However, as for the mice orally administrating two doses, 557 mg/kg or 2786 mg/kg of the composition of invention, the insulin levels increase by 24% and 36% (12.00±1.83 ng/dl and 13.7±2.31 ng/dl), respectively, when compared with that of the control group (9.69±2.04 ng/dl) (FIG. 5). In accordance with the recorded documents, insulin secretion is conducive to the protection of liver function.

Figure 6:
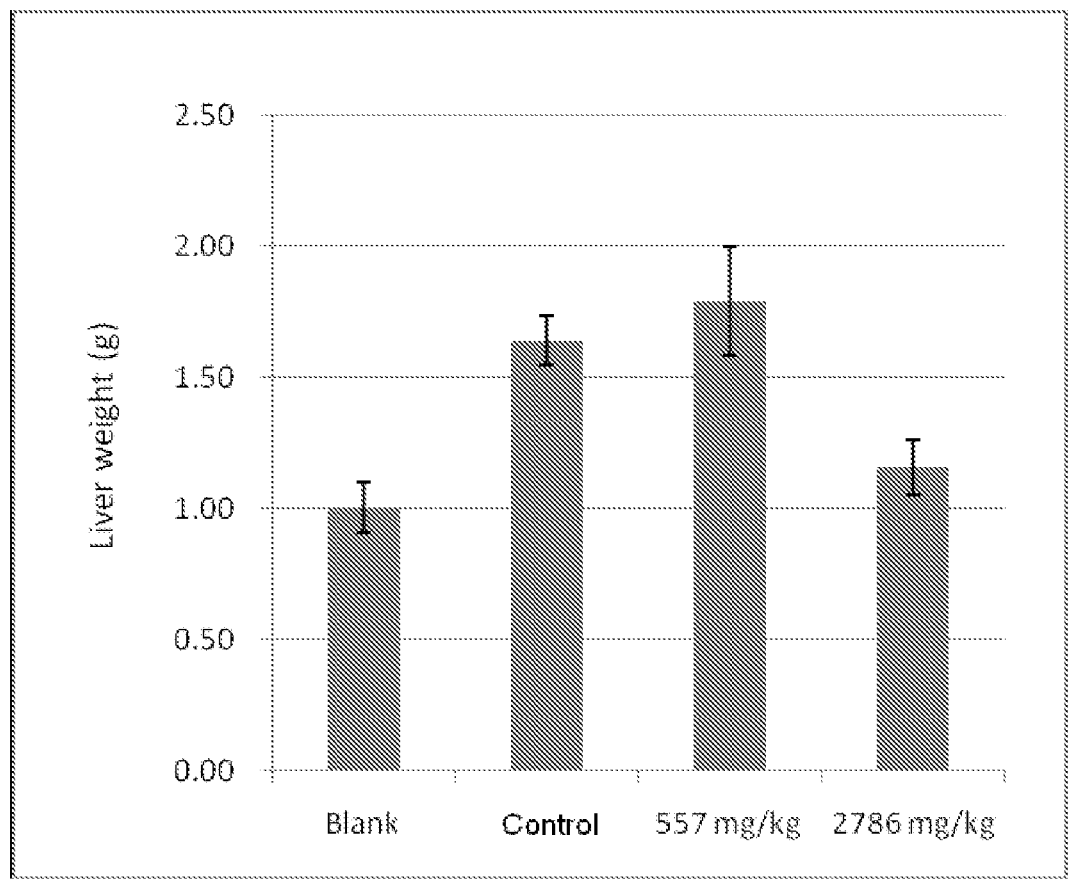
FIG. 6 shows the liver wet weight determined by an experiment of high fat diet induced fatty liver disease with four treatments.

Liver wet weight of the mice fed with high fat diet is higher than that of the blank group. After orally administering the mice with the composition of invention in the dose of 557 mg/kg for ten weeks, liver wet weight of the mice has no significant difference when compared with the control group. However, as for the mice orally administrating with the composition of invention in the dose of 2786 mg/kg, the liver wet weight decreases by about 29% when compared with that of the control group (1.16±0.1 g of the high dosage vs. 1.64±0.1 g of the control group) (FIG. 6).

The invention has been described hereabove with reference to the preferred embodiments and drawings, which should not be utilized to limit the scope of the invention. Therefore, various modification, omission and change of the above embodiments by the skilled person in the art are within the scope of the invention.

The invention claimed is:

1. A method for treating nonalcoholic fatty liver disease, comprising administering to a patient having nonalcoholic fatty liver disease, a composition comprising 50 to 90% by weight of *Cordyceps sinensis* mycelium, and 10 to 50% by weight of astragalus.

2. The method of claim 1, wherein the *Cordyceps sinensis* mycelium is *Paecilomyces hepiali* Chen et Dai mycelium.

3. The method of claim 1, wherein the *Cordyceps sinensis* mycelium is in a form of dry powder.

4. The method of claim 1, wherein the astragalus is a condensed astragalus powder made of a dried root selected from *Astragalus membranaceus* (Fisch.) Bge. Var. *mongholicus* (Bge.) Hsiao or *Astragalus membranaceus* (Fisch.) Bge.

5. The method of claim 1, wherein the composition is provided in a medicament or a health food.

6. The method of claim 5, wherein the medicament or the health food is an oral preparation in the form of capsules, tablets or powder.

* * * * *